United States Patent
Eyal

(12) 
(10) Patent No.: US 6,452,051 B1
(45) Date of Patent: Sep. 17, 2002

(54) PROCESS FOR THE PRODUCTION OF A CONDENSATION PRODUCTS OF A CARBOXYLIC ACID

(75) Inventor: Aharon M. Eyal, Jerusalem (IL)

(73) Assignee: Cargill, Inc.

( * ) Notice: Subject to any disclaimer, the term of this patent is extended or adjusted under 35 U.S.C. 154(b) by 0 days.

(21) Appl. No.: 09/125,033

(22) PCT Filed: Feb. 21, 1997

(86) PCT No.: PCT/US97/02156

§ 371 (c)(1),
(2), (4) Date: Oct. 30, 1998

(87) PCT Pub. No.: WO97/30964

PCT Pub. Date: Aug. 28, 1997

(30) Foreign Application Priority Data

Feb. 22, 1996 (IL) .................................................. 117232

(51) Int. Cl.⁷ ......................... C07C 69/66; C07C 231/00
(52) U.S. Cl. ......................... 564/136; 564/138; 560/179
(58) Field of Search ........................ 560/179; 564/136, 564/138

(56) References Cited

U.S. PATENT DOCUMENTS

| | | | | |
|---|---|---|---|---|
| 5,071,754 A | * | 12/1991 | Walkup et al. | .............. 435/135 |
| 5,142,023 A | | 8/1992 | Gruber et al. | .............. 528/354 |
| 5,252,473 A | * | 10/1993 | Walkup et al. | .............. 434/135 |
| 5,733,750 A | * | 3/1998 | Lund et al. | .................... 435/72 |

FOREIGN PATENT DOCUMENTS

WO          93/00440     *    1/1993

OTHER PUBLICATIONS

Advanced Organic Chemistry, 2nd edition, 1977, pp. 363–365, 1977.*

* cited by examiner

Primary Examiner—Barbara P. Badio
(74) Attorney, Agent, or Firm—Foley & Lardner

(57) ABSTRACT

The invention provides a process for the production of a condensation product selected from the group consisting of an amide and an ester of a carboxylic acid from an organic compound selected from the group consisting of organic compounds carrying a hydroxyl group and organic compounds carrying an amine group and from a concentrated medium resulting from fermentation, said medium containing a salt of the acid, the salt being selected from the group consisting of a sodium salt, a calcium salt, and mixtures thereof and the medium being at a pH of at least the pKa of the acid, the process comprising reacting the medium with the organic compound and with $CO_2$, whereby the condensation product and a salt selected from the group consisting of sodium carbonate, sodium bicarbonate, calcium carbonate, calcium bicarbonate, and mixtures thereof are formed; and, separating the condensation product from the reaction mixture formed in the previous step.

27 Claims, No Drawings

PROCESS FOR THE PRODUCTION OF A CONDENSATION PRODUCTS OF A CARBOXYLIC ACID

The present invention relates to a process for the production of a condensation product of carboxylic acid from a concentrated medium resulting from fermentation containing a salt of said acid. More specifically, the present invention is particularly useful as an important step in the production of a low cost esters especially in the production of lactic acid and in the production of biodegradable polylactic acid.

Carboxylic acids such as citric, lactic, succinic and malic acids can be produced by the continuous or batch fermentation of sugars, or other biomass streams, such as: hydrolyzed starch. Production is product inhibited and slows with pH reduction reaching a point at which said process is no longer practical. Product concentration in these solutions is in most cases very low, below 1%, and the high energy requirements of its concentration make the whole process uneconomical. In order to enhance fermentation, a base is added to maintain the pH at an optimal level, in most cases at about or somewhat higher than the pKa of the acid. More concentrated medium resulting from fermentation is obtained but said medium contains the salt of the acid rather than the free acid. Since in most cases the free form of the acid is the final product of interest, the substantial cost of acidulation is added. In many cases aciduation is performed by adding a strong mineral acid that displaces the carboxylic acid from the salt. Thus a base is consumed in the fermentation, a mineral acid in the acidulation and a salt is formed as an unwanted by-product. Lactic acid production, for example, uses a calcium base (mostly hydroxide) as the neutralizing agent. The medium resulting from fermentation obtained, containing calcium lactate, is treated with sulfuric acid to precipitate calcium sulfate and liberate the lactic acid. The latter is, however, left with most of the impurities present in the medium resulting from fermentation and requires additional operations for purification. Purification is typically performed by esterification in a reaction with an alkanol and distillation of the ester. The purified ester can be used as such or be hydrolysed to recover pure lactic acid and the alkanol.

Lactic acid has long been used as a food additive and in various chemical and pharmaceutical applications. More recently, lactic acid has been used in the making of biodegradable polymers both as a replacement for present plastic materials as well as various new uses in which biodegradability is needed or desired. Accordingly, there is an ever increasing demand for lactic acid. The present invention aims at meeting this demand by providing an efficient and low cost process for producing lactic acid esters or polyesters which avoids the consumption of bases and acids and substantially reduces, if not eliminates, the formation of waste salts.

Production of lactic acid is commonly carried out by fermentation of a strain of the bacterial genus Lactobacillus and more particularly by the species *Lactobacillus delbrueckii* or *Lactobacillus acidophilus*. The fermentation substrate consists of carbohydrates together with suitable mineral and proteinaceous nutrients. Because the lactic acid producing micro-organisms are inhibited in a strongly acidic environment, the pH of the fermentation broth must be kept above 5.0, and preferably within the rage of about 5.0 to 5.5. To maintain this pH level, suitable water-soluble basic substances that are non-toxic to the acid producing microorganism, such as alkali metal or alkaline earth-metal carbonates, are commonly added to the fermentation broth. This results in the formation of a lactate solution rather than the desired lactic acid product. Acidulation is thus required.

Various sources of lactic acid may be used for production of polylactic acid biodegradable polymer. These sources include, as disclosed in U.S. Pat. No. 5,142,023, lactic acid in solutions with hydroxylic medium such as water or other solvents, such as: low molecular weight alkanols and mixtures thereof. The source of lactic acid could also be an ester of lactic acid with a low molecular weight alkanol. The lactic acid source is first fed to an evaporator in which a portion of the water or solvent or any condensation reaction by-product is removed and optionally re-cycled. The evaporator thus concentrates the lactic acid causing some condensation. Oligomers and low molecular weight polymers start to form. The concentrated lactic acid is next fed to a pre-polymer reactor in which low molecular weight polylactic polymer is formed. The pre-polymer is then converted to the lactide which is purified and fed to a polymerization system in which the product is formed.

The present invention aims at producing lactic acid esters or polyesters (oligomers) suitable for use as lactic acid sources (as they are or after hydrolysis) in such a process.

Acidulation and esterification can be combined to one process as disclosed by Cockrem and Johnson (PCT, WO 93/00440). A fermentation broth containing ammonium lactate or another basic salt of lactic acid is acidified in the presence of an alcohol of 4–5 carbon atoms as a diluent using continuous addition of sulfuric acid or other strong acid and crystallizing to precipitate out some, or all, of the basic salt of the strong acid. This combined process, however, also consumes a base and a strong acid and produces a low value by-product.

The present invention applies $CO_2$ as a displacing acid which is surprising as $CO_2$ is about 7 orders of magnitude weaker than sulfuric acid used by Cockrem and also much weaker than carboxylic acids. Thus, in the present invention $CO_2$ is a reagent and is used in stoichiometric quantities during the esterification process. One aim of the present invention is to produce a condensation product selected from the group consisting of an amide and an ester of a carboxylic acid without the use of a base and a strong acid and to minimize the production of salts as by-products. The term ester as used herein in reference to the present invention, unless specified otherwise, is intended to include diesters, lactones, oligoesters and polyesters.

The present invention provides a process for the production of a condensation product selected from the group consisting of an amide and an ester of a carboxylic acid from an organic compound selected from the group consisting of organic compounds carrying a hydroxyl group and organic compounds carrying an amine group and from a concentrated medium resulting from fermentation, said medium containing a salt of said acid, said salt being selected from the group consisting of a sodium salt, a calcium salt and mixtures thereof and said medium being at a pH of at least the pKa of said acid, said process comprising:

(a) reacting said medium with said organic compound and with $CO_2$, whereby said condensation product and a salt selected from the group consisting of sodium carbonate, sodium bicarbonate, calcium carbonate, calcium bicarbonate and mixtures thereof are formed; and, (b) separating said condensation product from the reaction mixture formed in step a.

Reacting carboxylic acids with organic compounds carrying a hydroxyl group forms esters according to the equation:

$$RCOOH + R'OH = RCOOR' + H_2O$$

If any of the reagents or both of them are polyfunctional so that a hydroxyl group or a carboxylic group are present on the ester, the latter could further react to form diester and higher esters. In a similar way reacting of a carboxylic acid with organic compounds carrying a primary or a secondary amine group forms amides, dimides or higher amides according to the following equation:

$$RCOOH + R'NH_2 = RCONHR' + H_2O$$

Both ester formation and amide formation are referred to in the general term: condensation reactions; esters and amides are referred to as condensation products. Both reactions of carboxylic acids involve, in most cases, water formation and are enhanced by lowering the water content in the reaction medium as well as by removing the by-product water from the reaction medium. Low water content can be achieved by operating in a solvent phase, using highly concentrated aqueous solutions of the reagents and/or adding other components (soluble or insoluble), which are highly hydrophilic and compete for the available water. Both reactions are usually conducted at elevated temperatures, preferably in the presence of a catalyst.

In most cases both the ester and the amide are more volatile than the carboxylic acid forming them, which allows purification by distillation. In both cases, reacting the condensation product with water in a system with high water activity reverses the reaction. The condensation product is hydrolyzed reforming the carboxylic acid and the organic compound carrying the hydroxyl group or the organic compound carrying the amine group. Those could be separated to form a pure carboxylic acid and a reagent that can be reused in the condensation reaction.

In those cases where another ester or amide is the desired product, the carboxylic acid formed on the hydrolysis could be reacted again with a suitable alkanol or amine. Yet, in many cases the hydrolysis can be avoided. The condensation first product can be reacted with a hydroxyl group carrying compound (R'OH) or an amine carrying compound (R'NH$_2$) to directly form the desired product and to reform the reagent. Thus, RCOOR' can be reacted with R"OH and RCONHR' reacted with R"NH$_2$ according to the following equation:

$$RCOOR' + R"OH = RCOOR" + R'OH$$

OR $$RCONHR' + R"NH_2 = RCONHR" + R'NH_2$$

where RCOOR" or RCONHR" are the desired product and R'OH or R'NH$_2$ can be reused in the first step. This reaction is driven forward by removal of R'OH and RNH$_2$ from the reaction mixture. Furthermore, RCOOR' can be reacted with R"NH$_2$ to form RCONHR" and R'OH and RCONHR' can be reacted with R"OH to form RCOOR" and R'NH$_2$.

In especially preferred embodiments of the present invention there is provided a process for the production of an ester of a carboxylic acid from an organic compound carrying a hydroxyl group and from a concentrated medium resulting from fermentation containing a salt of said acid, said salt being selected from the group consisting of a sodium salt, a calcium salt and mixtures thereof and said medium being at a pH of at least the pKa of said acid, said process comprising:

(a) reacting said medium with said organic compound and with CO$_2$, whereby said ester and a salt selected from the group consisting of sodium carbonate, sodium bicarbonate, calcium carbonate, calcium bicarbonate and mixtures thereof are formed; and, (b) separating said ester from the reaction mixture.

Said process is useful in a low cost production of esters of carboxylic acids such as citric, lactic, succinic and malic. More specifically, the present invention is particularly useful as an important step in production of a low cost lactic acid and in the production of the biodegradable polylactic acid.

Walkup et. al. (U.S. Pat. Nos. 5,071,754 and 5,252,473) disclose a process for forming lactic acid esters providing for base re-cycle and avoiding the consumption of a strong acid and the formation of by-product salts.

Walkup uses ammonia as a base in fermentation and ammonium lactate is obtained. Alcohol is added to the ammonium lactate solution and further catalyzing amounts of gaseous CO$_2$ is applied to produce lactate ester which is separated and purified by distillation.

One of the important factors in the efforts to achieve a low-cost lactic acid is to recover and recycle the base. According to the Walkup U. S. patents, ibid. this is done by the distillation of the gaseous ammonia, but it is admitted (Column 8, Line 52) that recycling may not be justified and that there are some difficulties in recovering the ammonia in a sufficiently pure form. There are some additional disadvantages in Walkups' processes. Ammonia tends to form amides with lactic and other carboxylic acids at the temperatures and dehydrating conditions used in Walkup's patents. Furthermore, it is not convenient to establish a synthetic production with ammonia as it is a gas with a well-known unpleasant smell. In contradistinction, it is suggested in the present invention to use sodium or calcium salt instead of the ammonium salt and thus carbonate or bicarbonate of sodium or calcium are formed and can easily be separated, purified and further used in fermentation. Moreover, Walkup's process is comprised of two main steps. The first step is converting the lactic acid salt (ammonium lactate) to lactic acid and NH$_3$, and the second step is the esterification of lactic acid. According to Walkup, the conversion rate is controlled by the first step which has a low equilibrium constant. In the present invention the lactate salts are of bases much stronger than ammonia and thus the high conversion achieved by the process of the present invention is surprising.

Walkup uses CO$_2$ as a catalyst. This is clearly shown in his data summarized in his FIG. 2. Substantial yields are obtained in the absence of CO$_2$ under nitrogen atmosphere at 150° C. Pressurization with CO$_2$ at the same temperature does increase yields, but in most cases by less than 20%. In the present invention CO$_2$ is a reagent and preferably is used in amounts of about or higher than equivalent to the carboxylic acid salt in the medium resulting from fermentation. In clear distinction from Walkup the present invention is impractical without CO$_2$.

Walkup discloses (Column 8, Lines 15–21) that polymers are not formed in his process. The present invention provides for the production of polyesters.

As stated, the present invention relates to a low cost process for production of esters. The invention is applicable for esters formed from any combination of salts of hydroxycarboxylic, dicarboxylic and polycarboxylic acids and alkanols, diols or polyols (organic compounds carrying two or more hydroxyl groups). The term "carboxylic acid" includes also a hydroxy carboxylic acid, diacids and polyacids. Suitable carboxylic acids are citric, lactic, succinic and malic acid. The present description will be focused on lactic acid without limiting the scope of the invention.

The concentrated medium resulting from fermentation comprising sodium or calcium salt of the carboxylic acid is at a pH close to or above the pKa of the acid. The organic compound carrying the hydroxyl group can be lactic acid, glycolic acid or their sodium or calcium salts.

In the first step of the process according to the present invention, said medium resulting from fermentation and said hydroxyl group carrying organic compound are reacted with $CO_2$ whereby the ester is formed and carbonate or bicarbonate of sodium or calcium are formed. In the second stage of said process the ester is separated from the reaction mixture. The reaction temperature is preferably from approximately 20° C. to 200° C. The reaction pressure is preferably 5 atmospheres to about 100 atmospheres.

The process according to the invention may have an additional step of hydrolyzing the separated ester to form high purity acid.

In a preferred embodiment a solvent is present in the reaction, said solvent being substantially immiscible in said medium resulting from fermentation, and a good solvent of the ester formed. The ester formed from an acid salt and from said organic compound is less hydrophilic than the acid salt forming it. As a result, it selectively fractionates into a solvent, if present in the system. This selective fractionation shifts the reaction equilibrium toward the product and improves conversion. It also provides means of separating the product from the reaction mixture. This solvent should have low volatility in the reaction temperature and pressure. It should be substantially immiscible with the concentrated medium resulting from fermentation in these conditions. Ethers, aldehydes, ketones and other solvents, particularly those used in the food industry are suitable.

In a particularly preferred embodiment, most of the ester is present in the solvent phase and is recovered from that phase after it is separated from the aqueous solution and from the bicarbonate or carbonate. Product separation from the solvent can be performed in well known methods, including distillation, precipitation and addition of non-solvents. It is particularly preferred to perform the separation by distillation of the product or the solvent. The boiling points of the product and the solvent should differ by about 10° C. or more.

In a preferred embodiment the hydroxyl group carrying organic compound, particularly, an alkanol, has relatively low solubility in the concentrated medium resulting from fermentation and, when used in excess, forms a separate phase acting as a solvent for the product. Alkanols of three carbon atoms and more are suitable.

In a preferred embodiment, an esterification catalyst is used in the reaction. Strong acids are not desired as they may interfere with bicarbonate or carbonate production. Neutral catalysts such as aluminium sulfate are preferred.

In another preferred embodiment, the catalyst is an enzyme. Proteases, esterases and lipases are examples of suitable enzymes.

Hydroxycarboxylic acid comprise both a hydroxyl and a carboxyl group and can therefore act as both the acid source and hydroxyl source for esterification. Alkanol is not required as a reagent. Intermolecular reactions in concentrated medium resulting from fermentation containing salts of hydroxycarboxylic acid need only $CO_2$ as a reagent to form the diester and the corresponding carbonate or bicarbonate. The diester formed has a hydroxyl and a carboxyl group and can further react. It may form an intramolecular esterification to lactone (lactide in the case of lactic acid) or react with more $CO_2$ and additional hydroxycarboxylic acid salt molecules to form oligomers and higher polyesters.

Ester formation from an acid and a hydroxyl carrying organic compound form water as a by-product according to the equation:

$$RCOOH + ROH \leftrightarrows RCOOR + H_2O$$

Water present in the system therefore drives the esterification backward and should therefore be limited, in a preferred embodiment of the process, the medium resulting from fermentation used in the process is in concentration of about 40% w/w or higher. These concentrations are not reached in fermentation in most cases and medium resulting from fermentation should be concentrated by water evaporation. Other pre-treatments may be helpful such as filtration, ultrafiltration and carbon treatment.

In a preferred embodiment, water is removed from the system by the addition of water absorbing agents or by distillation. Low molecular weight alkanols such as ethanol have a similar effect. If the hydroxyl carrying organic compound is a low molecular weight alkanol it can be used in an excess, driving the reaction forward also by binding water in the system and reducing its activity.

Water is formed as a by-product in the process described in U.S. Pat. No. 5,071,754, and U.S. Pat. No. 5,252,473.

$$NH_4Lactate \leftrightarrows NH_3 + LacticAcid$$

$$LacticAcid + ROH \leftrightarrows ROLactate + H_2O$$

Similarly water is formed in WO 93100440

$$2NH_4Lactate + 2ROH + H_2SO_4 = 2\ ROLactate + (NH_4)_2SO_4 + 2H_2O$$

The water formed adds to the water in the medium resulting from fermentation and hinders esterification. An effort should be made for water removal. In a clear distinction in the process of this invention, as $CO_2$ is used as a reagent rather than as a catalyst, water does not form on bicarbonate formation as can be seen from the following reaction scheme:

$$NaLactate + CO_2 + ROH = ROLa + NaHCO_3$$

$$Ca(Lactate)_2 + CO_2 + 2ROH = 2ROLa + Ca(HCO_3)_2$$

or is formed in just half the equivalent amount if a carbonate is formed as follows:

$$Ca(Lactate)_2 + CO_2 + 2ROH \leftrightarrows 2ROLa + CaCO_3 + H_2O$$

Fermentative production of many carboxylic acids is product inhibited and slows with pH reduction, reaching a point at which it is no longer practical. A basic compound is added as a neutralizing agent to maintain the pH at an optimal level, in most cases at about or somewhat higher than pKa of the acid. As a result, the medium resulting from fermentation contains mainly the salt of the acid rather than the free acid. Bases such as bicarbonate, carbonate or hydroxide of sodium and calcium are particularly suitable.

In a preferred embodiment of the process of the present invention the carbonate or bicarbonate of calcium or sodium formed in the reaction is separated, purified and used as a neutralizing agent in the fermentation. Sodium bicarbonate and particularly calcium carbonate have low water solubility and precipitate out of the reaction mixture. Separation can be assisted by methods known in the art including cooling, removal of the solvent, or, in the case of using calcium bases in fermentation, release of $CO_2$ pressure after product removal. The separated bicarbonate or carbonate are suitable for use as neutralizing agents in the fermentation as they are or after purification and treatment. Calcium carbonate, for example, can be calcined to calcium oxide which, preferably after conversion to calcium hydroxide, is the preferred neutralizing agent in many fermentation processes. Sodium bicarbonate is easily converted to soluble sodium carbonate by heating in water. The resulting solution or a part of it can be purified if required, for example by carbon treatment.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

100 gr. of filtered, sodium lactate containing, medium resulting from fermentation were concentrated from about 10% salt to about 50% salt through water evaporation. 75 gr. of ethanol was added and the mixture was introduced into a pressure reactor. Gaseous $CO_2$ was added and was observed to be absorbed in the reaction mixture. More $CO_2$ was added until the pressure stabilized at 40 atmospheres. The temperature was elevated to 100° C. and the reaction mixture was stirred for 5 hours. The pressure and temperature were then lowered and the vessel was opened. The amount of sodium bicarbonate and ethyl lactate found, show that a major part of the sodium lactate was converted to sodium bicarbonate and ethyl lactate. The sodium bicarbonate is filtered and converted to soluble sodium carbonate treated by active carbon and is suitable for use in fermentation.

EXAMPLE 1a—A Comparative Example

The experiment in example 1 was repeated using nitrogen as the gas instead of $CO_2$. No substantial absorption was observed and bicarbonate and ethyl lactate were not detected.

EXAMPLE 2

The experiment in Example 1 was repeated with few changes. The medium resulting from fermentation contained calcium lactate that was concentrated to 30%. The amount of ethanol was increased to 120 gr. and the final $CO_2$ pressure was 30 atmospheres. Here again, high conversions were found.

EXAMPLE 3

The experiment in Example 1 was repeated with two differences. The sodium lactate concentration in the concentrated broth was elevated to 80% and methyl isobutyl ketone was introduced instead of ethanol. Poly lactic acid was found in the solvent phase at the end of the experiment.

EXAMPLE 4

The experiment in Example 3 was repeated with butyl amine instead of methyl isobutyl ketone and at 140° C. Butyl lactide amide was found at the end of the reaction.

EXAMPLE 5

Filtered sodium lactate solution resulting from fermentation was concentrated to form 45 g. solution of 75% sodium lactate. This solution was introduced into a pressure vessel together with 75 g. butanol and 0.016 San(II) ethyl hexanoic acid. Gaseous $CO_2$ was introduced and was observed to be adsorbed in the reaction mixture. More $CO_2$ was added to reach 21 atmospheres and the temperature was elevated to 145° C. while stirring. After 3 hours, a sample of the upper phase was taken, the pressure and the temperature were lowered and the vessel was opened. Three phases were found: a large solid phase composed of sodium bicarbonate, some aqueous phase and an organic phase. An HPLC analysis of this organic phase show that it contained about 0.3 mol/Kg. of butyl lactate and about that concentration of lactic acid.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the production of a condensation product selected from the group consisting of an amide and an ester of a carboxylic acid from an organic compound selected from the group consisting of organic compounds carrying a hydroxyl group and organic compounds carrying an amine group and from a concentrated medium resulting from fermentation, said medium containing a salt of said acid, said salt being selected from the group consisting of a sodium salt, a calcium salt and mixtures thereof and said medium being at a pH of at least the pKa of said acid, said process comprising:

(a) reacting said medium with said organic compound and with $CO_2$, said $CO_2$ functioning in said reaction to displace the carboxylate anion from said sodium and calcium carboxylic salts, whereby said condensation product and a salt selected from the group consisting of sodium carbonate, sodium bicarbonate, calcium carbonate, calcium bicarbonate and mixtures thereof are formed; and, (b) separating said condensation product from the reaction mixture formed in step a.

2. A process according to claim 1, for the production of an ester of a carboxylic acid from an organic compound carrying a hydroxyl group and from a concentrated medium resulting from fermentation containing a salt of said acid, said salt being selected from the group consisting of a sodium salt, a calcium salt and mixtures thereof and said medium being at a pH of at least the pKa of said acid, said process comprising:

(a) reacting said medium with said organic compound and with $CO_2$, whereby said ester and a salt selected from the group consisting of sodium carbonate, sodium bicarbonate, calcium carbonate, calcium bicarbonate and mixtures thereof are formed; and, (b) separating said ester from the reaction mixture.

3. The process of claim 1, wherein said organic compound is selected from the group consisting of alkanols, hydroxy carboxylic acids and salts thereof.

4. The process of claim 1, wherein the reaction is carried out at a temperature of between about 20° C. and 200° C.

5. The process of claim 1, wherein the reaction is carried out at a pressure of about 5 atmospheres to about 100 atmospheres.

6. The process of claim 3, wherein said alkanol is selected from the group consisting of methanol, ethanol, propanol, isopropanol, butanol and isobutanol.

7. The process of claim 1, wherein said carboxylic acid is a hydroxy carboxylic acid.

8. The process of claim 1, wherein said organic compound is selected from the group consisting of lactic acid, glycolic acid and salts thereof.

9. The process of claim 1, wherein said carboxylic acid is selected from the group consisting of lactic acid, citric acid, malic acid and succinic acid.

10. The process of claim 9, wherein said carboxylic acid is lactic acid.

11. The process of claim 2, wherein said carboxylic acid is lactic acid and said ester is a lactic acid ester.

12. The process of claim 11, wherein said lactic acid ester is a product of the reaction of at least two lactic acid molecules.

13. The process of claim 12, wherein said ester is selected from the group consisting of lactide, lactoyl lactate, lactic acid oligomers and polylactic acid.

14. The process of claim 2, wherein said organic compound is a lactic acid salt, said salt being selected from the group consisting of the sodium salt, the calcium salt and mixtures thereof.

15. The process of claim 1, wherein the pH of said fermentation is maintained by the introduction of a neutralizing agent selected from the group consisting of sodium carbonate, sodium bicarbonate, calcium carbonate, calcium bicarbonate, sodium hydroxide, calcium hydroxide and mixtures thereof.

16. The process of claim 15, wherein said salt formed in step (a) is separated and used as a neutralizing agent in said fermentation.

17. The process of claim 1, wherein said salt precipitates in step (a).

18. The process of claim 2, further comprising hydrolyzing the separated ester to form high-purity acid.

19. The process of claim 2, further comprising converting said ester to polylactic acid.

20. The process of claim 1, further comprising water removal.

21. The process of claim 1, wherein a condensation catalyst is used in the reaction.

22. The process of claim 21, wherein said catalyst is an enzyme.

23. The process of claim 2, wherein at least one solvent is present in the reaction, said solvent being substantially immiscible in said medium resulting from fermentation and being a good solvent for the ester formed.

24. The process of claim 23, wherein said solvent is said organic compound when present in above-stoichiometric amounts.

25. The process of claim 23, wherein said ester is recovered from a phase formed by said solvent.

26. The process of claim 25, wherein said ester is recovered from said solvent phase by distillation.

27. The process of claim 1, wherein the concentration of the salt in the medium resulting from fermentation is at least 40% w/w.

* * * * *